United States Patent [19]

Whitefield

[11] Patent Number: 5,061,486

[45] Date of Patent: Oct. 29, 1991

[54] DITHRANOL COMPOSITION CONTAINING NO OILY INGREDIENTS

[75] Inventor: Martin Whitefield, London, England

[73] Assignee: Drythanol Ltd., London, England

[21] Appl. No.: 512,906

[22] Filed: Apr. 25, 1990

Related U.S. Application Data

[63] Continuation of Ser. No. 286,736, Dec. 20, 1988, abandoned.

[30] Foreign Application Priority Data

Dec. 22, 1987 [GB] United Kingdom ............... 8729855

[51] Int. Cl.$^5$ ............................................. A61K 31/78
[52] U.S. Cl. ........................................ 424/81; 424/78; 514/732; 514/863
[58] Field of Search .................... 424/81, 78; 514/863, 514/732

[56]  References Cited

U.S. PATENT DOCUMENTS 4,287,214  9/1981  Van Scott et al. .
4,551,480 11/1985  Stejel .................................. 514/863

FOREIGN PATENT DOCUMENTS 0006724  1/1980  European Pat. Off. .
 659945  6/1984  Fed. Rep. of Germany .
2524313 10/1981  France .
1574090  6/1977  United Kingdom .
2142534  1/1985  United Kingdom ............... 514/863
2163956  3/1986  United Kingdom .
2188844 10/1987  United Kingdom .

OTHER PUBLICATIONS

Grant & Hach's Chem. Dictionary 5th Edition, p. 212, McGraw Hill Co.
European Search Report, Vienna, 02-14-89, Mazzucco.
The Journal of Investigative Dermatology, 64:145-149, 1975, vol. 64, No. 3.

*Primary Examiner*—John Doll
*Assistant Examiner*—E. J. Kraus
*Attorney, Agent, or Firm*—Stevens, Davis, Miller & Mosher

[57]  ABSTRACT

The invention provides novel compositions for topical application, e.g. for the treatment of psoriasis, comprising finely divided dithranol dispersed in a thickened aqueous medium.

10 Claims, No Drawings

DITHRANOL COMPOSITION CONTAINING NO OILY INGREDIENTS

This application is a continuation of application Ser. No. 286,736, filed Dec. 20, 1988, now abandoned.

This invention relates to compositions for topical application to the skin containing dithranol.

Dithranol (1,8-dihydroxy-9-anthrone, also known as anthralin) is widely used for the treatment of psoriasis, for which purpose it is applied directly to the psoriatic lesions. It suffers from two practical disadvantages, namely that it is readily oxidised by oxygen in the air to inactive materials; and that its oxidation products very easily stain clothing and bed linen with which they come into contact.

There have been a number of references in the literature to compositions containing dithranol which are said to possess advantages over previously known compositions. For example, in our British Specification No. 1575090 we have described compositions for topical application in the treatment of psoriasis comprising dithranol, a water-soluble acid and anti-oxidant, petroleum jelly, an emulsifier and water. This composition forms a cream which, when correctly applied to the psoriatic areas, and thoroughly rubbed into the lesions, reduces the likelihood and intensity of staining of clothing and bed linen after application. U.S. Pat. No. 4,551,480, assigned to Stiefel Laboratories Inc. describes cream compositions containing, in addition to dithranol, a water-in-hydrocarbon emulsion, an anionic emulsifier, an oil-soluble antioxidant, an acid, and a sequestering agent. However, the compositions of these two specifications, like other known dithranol-containing compositions, in practice, still exhibit the distinct propensity to stain clothing to an unacceptable degree, and this severely limits their use by patients. There is, therefore, a need for a dithranol-based composition having a very substantially reduced tendency to stain, whilst retaining activity against psoriasis.

In the known compositions, the dithranol, which is highly insoluble in water, is dissolved, or at least dispersed, in an oily medium, and it has been thought that use of such a medium is essential if the dithranol is to be effective.

We have now unexpectedly discovered that dithranol may be incorporated in an aqueous medium containing no oily ingredients, whilst retaining therapeutic activity, to provide a composition having a very substantially reduced tendency to stain clothing or other material with which it comes into contact.

The pharmaceutical compositions of the present invention comprise very finely divided solid dithranol dispersed in a single phase aqueous or aqueous alcoholic medium comprising, in solution, a water-soluble chelating agent, e.g. the disodium salt of ethylene diamine tetra acetic acid, a water-soluble antioxidant, e.g. ascorbic acid, and a water-soluble thickener or gelling agent. A water-soluble humectant, e.g. sorbitol, propylene glycol or glycerol, is preferably also present. The composition does not contain any non-volatile emulsifier. The dispersion of the dithranol in the medium is facilitated when a small proportion of alcohol (up to 30%) is present. When the composition is used, i.e. applied to a psoriatic lesion, the solvent medium, i.e. water or aqueous alcohol, rapidly evaporates leaving behind the finely divided solid dithranol itself together with the chelating agent and anti-oxidant which serve to stabilise the dithranol, and the humectant (when present) and the thickener or gelling agent.

The inclusion in the compositions of a water-soluble humectant, usually in a proportion up to 15% by weight of the composition, may be advantageous to counteract the rather drying tendency which an aqueous alcoholic medium has on the skin. Any such humectant must not constitute (at the concentration used) a solvent for the dithranol since the activity, stability and non-staining properties of the new composition depend upon providing the dithranol in solid, finely divided form and not in solution.

The proportion of dithranol present in the new compositions may vary within wide limits. Since dithranol is active in very low concentration, a proportion as low as 0.025% by weight of the total composition may in some circumstances be sufficient. The upper limit of the effective range of concentration depends upon the need to prevent too great an irritant effect on normal skin and to provide a composition which has satisfactory storage-stability. In practice, there is unlikely to be any advantage in including more than 10% by weight of dithranol in the composition. The effective concentration range is usually from 0.1 to 5.0% by weight. The dithranol should be very finely divided, i.e. pass substantially completely through a sieve having a nominal mesh aperture size of 125 micrometers ($\mu$m), and the preferred particle size of the dithranol is 10 to 30 micrometers. Dithranol having this particle size is available commercially or can be made by grinding coarser samples of dithranol taking precautions to avoid oxidation.

In the new compositions, the dithranol is stabilised by a combination of water-soluble chelating agent and a water soluble anti-oxidant. The water-soluble chelating agent is preferably the disodium salt of ethylene diamine tetra acetic acid. It may be present in a proportion of 0.02 to 0.1% by weight of the composition preferably 0.05%. The water-soluble antioxidant is preferably ascorbic acid or a water-soluble ascorbate, e.g. sodium ascorbate, which may be present in a proportion of 0.02 to 0.5%, preferably 0.2% by weight, amounts lower than this normally providing inadequate stabilisation, and amounts higher than 0.2% not normally providing any advantage. Salicylic acid may also be used in low concentration, e.g. 0.05 to 0.5% by weight of the composition. Both the chelating agent and the anti-oxidant are dissolved in the aqueous alcoholic medium. The compositions of the invention are acidic and have a pH between 2.5 and 5.0 preferably in the range 2.5 to 4.5. Compositions with a pH above 5 have inferior storage stability unless air (oxygen) is rigorously excluded, while those below 2.5 are not pharmaceutically acceptable.

The new compositions are thickened with a water-soluble thickener or gelling agent in order that the finely divided dithranol shall not separate from the composition. Preferably the concentration of the thickener or gelling agent is 1.0 to 3.0% by weight of the composition.

For prolonged stability of the dithranol, it is especially preferred to use a thickener or gelling agent which is acidic. A suitable example is carbomer, e.g. Carbopol 940 (B. F. Goodrich) which is a polyacrylic acid (carboxyvinyl polymer). By itself, such a polymer only increases the viscosity slightly. In order to achieve an actual gel the acidic carboxyl groups have to be neutralised or partially neutralised using a suitable alkaline substance which produces a soluble salt. For aqueous or aqueous alcoholic systems, potassium hydroxide is preferably used for this purpose. The polymer is conveniently incorporated as the free carboxylic acid which produces a pH of around 3. Dilute aqueous potassium hydroxide is added very slowly with continuous mixing until the pH rises to between 3.5 and 4.5, preferably about 4. At this pH, the gel is sufficiently viscous to provide a homogeneous dispersion of the dithranol in a semi-solid medium while still being sufficiently acid to provide stability of the dithranol.

Other water-soluble thickeners or gelling agents which are stable at physiologically acceptable acid pH and compatible with the dithranol and other ingredients may also be used, e.g. hydroxy ethyl cellulose or other water-soluble cellulose derivative. With such materials the compositions preferably have a pH between 2.5 and 3.5, especially about 3.

The aqueous alcoholic medium is preferably aqueous ethanol in which the alcohol concentration is 5 to 30% by weight of the total composition. The alcohol chosen should, of course, be substantially non-toxic at the contemplated rates of application of the compositions. Industrial methylated spirit or isopropyl alcohol may also be used. The alcohol chosen must have sufficient wetting action on the water-insoluble dithranol to ensure that the latter is homogeneously dispersed in the aqueous medium.

The new compositions may be used in essentially the same way as known dithranol containing compositions except that it is possible to take advantage of their substantially reduced tendency to stain. Thus, the new compositions may be applied to psoriatic areas which come into contact with clothing and bed linen with much more confidence that the latter will not be unacceptably stained by oxidation products of the dithranol. Since the new compositions contain no oily ingredients, when they are applied to the skin, and the solvents (water and alcohol) have evaporated, the only residue remaining consists of the dithranol itself, still in finely divided form, and the chelating agent, anti-oxidant, humectant and gelling agent. The proportions of the latter are so small that the amount of residue of the composition which remains is practically negligible. The lack of staining properties of the new compositions also means that they are substantially less likely to cause staining of bathing equipment, such as baths or showers, or of the hair.

While the new compositions have been described primarily in relation to their utility in the treatment of psoriasis (for which purpose they are used in essentially the same way as known dithranol-based anti-psoriatic compositions), it has previously been proposed to use dithranol in the treatment of a wide variety of other skin conditions (see Beerman et al., J. Amer. Med. Assoc., 104, 26-29, 1935, where it is referred to as dioxyanthranol 1-8), and it is believed that the new compositions will improve the acceptability of dithranol for use in the treatment of such conditions, which include cutaneous mycoses, chronic eczema, alopecia, and viral skin infections, particularly herpes. Although dithranol is reported to be effective in the treatment of these skin conditions, its side effects of irritation and staining have previously been thought to render it unsuitable for general use. The new compositions, by making it possible to formulate dithranol in much lower concentrations than has previously been thought practical, greatly increases the opportunity of using dithranol in such conditions.

If desired other active ingredients compatible with dithranol and suitable for topical application may be included in the new compositions, for example anti-inflammatory agents.

The following Examples illustrate compositions in accordance with the invention.

EXAMPLE 1

A composition was made comprising, in percent by weight based on the total weight of the composition:

| | |
|---|---|
| Dithranol (10 to 30 $\mu$m) | 0.1 to 5.0% |
| Disodium Salt of Ethylene Diamine Tetra Acetic Acid (EDTA) | 0.05% |
| Ascorbic Acid | 0.2% |
| Propylene glycol (optional) | 5.0% |
| Sorbitol | 5.0% |
| Alcohol | 20.0% |
| Carbomer (Carbopol 940) of B. F. Goodrich Ltd. | 1.5% |
| 1.0 M Potassium Hydroxide Solution | 3.0% |
| Purified Water | to 100% |

The EDTA, the ascorbic acid, and the sorbitol and propylene glycol (when used) are dissolved in the water which is then mixed with the alcohol. The carbomer is then added gradually and mixed in thoroughly until wetted and dispersed. This forms a mucilage which is allowed to stand for at least 3 hours in order to allow full swelling of the polymer. The dithranol is then added under nitrogen and thoroughly dispersed. The potassium hydroxide solution is then added very slowly and mixing continued until it has completely reacted with the carbomer and the mixture has thickened to a semi-solid gel. The final pH is 3.5 to 4.5. The gel is packed immediately into membraned collapsible aluminium tubes which are sealed.

EXAMPLE 2

A composition was made comprising, in percent by weight based on the total weight of the composition:

| | |
|---|---|
| Dithranol (10 to 30 $\mu$m) | 0.1 to 2% |
| Disodium salt of Ethylene Diamine Tetra Acetic Acid (EDTA) | 0.05% |
| Ascorbic acid | 0.2% |
| Glycerol | 4.0% |
| Alcohol | 20.0% |
| Hydroxyethyl cellulose (Natrosol 250 HHR of Hercules Ltd.) | 2.0% |
| Salicylic acid (optional) | 0.2% |
| Water | to 100% |

The EDTA, the salicylic acid (if used), and the ascorbic acid are dissolved in a mixture of the glycerol, the alcohol, and about half the water at 60° C. The dithranol is then added and the mixture is thoroughly stirred with a homogenising stirrer. The remainder of the water is then added while the temperature is kept at 60° C. The hydroxy ethyl cellulose is then added and mixing is continued until it has completely dispersed and the mixture has thickened to a semi-solid gel. The final pH is 2.5 to 3.5. The gel is packed immediately into membraned collapsible aluminium tubes which are sealed.

The stability of the composition is slightly improved when the salicylic acid is incorporated.

I claim:

1. A pharmaceutical composition for topical application to the skin comprising very finely divided dithranol dispersed in a single phase aqueous medium containing no oily ingredients comprising, in solution, a water-soluble chelating agent, a water-soluble antioxidant, and a water-soluble thickener or gelling agent.

2. A composition according to claim 1 which also includes a water-soluble humectant in which dithranol is substantially insoluble.

3. A composition according to claim 2 in which the humectant is sorbitol, propylene glycol or glycerol or a mixture thereof.

4. A composition according to claim 1 having a pH of 2.5 to 5.

5. A composition according to claim 1 in which the thickener or gelling agent is a polyacrylic acid or a water-soluble cellulose derivative.

6. A composition according to claim 1 in which the water soluble chelating agent is the disodium salt of ethylene diamine tetra acetic acid.

7. A composition according to claim 1 comprising:

| Dithranol | 0.025–10.0 percent by weight |
| --- | --- |
| Water-soluble Chelating Agent | 0.02–0.1 percent by weight |
| Antioxidant | 0.02–0.5 percent by weight |
| Thickener or gelling agent | 1.0–3.0 percent by weight |
| Humectant | 0–15.0 percent by weight |
| Alcohol | 5.0–30.0 percent by weight |
| Water | to 100 |

8. A composition according to claim 1 in which the water-soluble antioxidant is ascorbic acid.

9. A composition according to claim 1 in which the dithranol has a particle size of 10 to 30 micrometers 10. A composition according to claim 1 comprising:

| Dithranol having a particle size of 10 to 30 micrometers | 0.025 to 10.0 percent by weight |
| --- | --- |
| Disodium salt of ethylene diamine tetra acetic acid | 0.02–0.1 percent by weight |
| Ascorbic acid | 0.02–0.5 percent by weight |
| Polyacrylic acid or water soluble cellulose derivative | 1.0 to 3.0 percent by weight |
| Sorbitol, propylene glycol, or glycerol | 0 to 15.0 percent by weight |
| Alcohol | 5.0 to 30.0 percent by weight |
| Water | to 100 percent. | the said composition having a pH of 2.5 to 5.

* * * * *